US 6,690,961 B1
Feb. 10, 2004

(12) United States Patent
Kaufman et al.

(54) APPARATUS AND METHOD FOR TRANSITION BETWEEN FLUORO-MODE AND DIAGNOSTIC MODE MAGNETIC RESONANCE IMAGING

(75) Inventors: Leon Kaufman, San Francisco, CA (US); Christine Hawryszko, Redwood City, CA (US)

(73) Assignee: Toshiba America MRI, Inc., Tustin, CA (US)

( * ) Notice: Subject to any disclaimer, the term of this patent is extended or adjusted under 35 U.S.C. 154(b) by 0 days.

(21) Appl. No.: 09/570,693

(22) Filed: May 12, 2000

(51) Int. Cl.⁷ .............................................. A61B 5/055
(52) U.S. Cl. ........................ 600/410; 324/318; 324/307; 324/309
(58) Field of Search ................................. 600/407, 408, 600/410, 411, 413, 415, 425, 427, 428, 420; 324/307, 309, 318, 322; 128/920, 922, 923, 924, 925; 382/128, 131; 705/2, 3; 378/21, 4, 42; 250/363.04, 370.08, 370.09

(56) References Cited

U.S. PATENT DOCUMENTS

| | | | |
|---|---|---|---|
| 4,830,012 A | | 5/1989 | Riederer |
| 4,982,161 A | | 1/1991 | Twieg |
| 5,155,435 A | * | 10/1992 | Kaufman et al. ............ 324/309 |
| 5,184,074 A | * | 2/1993 | Kaufman et al. ............ 324/309 |
| 5,365,927 A | * | 11/1994 | Roemer et al. ............. 324/309 |
| 5,423,315 A | * | 6/1995 | Margosian et al. ......... 324/309 |
| 5,512,826 A | | 4/1996 | Hardy et al. |
| 5,519,320 A | | 5/1996 | Kanayama et al. |
| 5,584,293 A | * | 12/1996 | Darrow et al. .............. 324/309 |
| 5,713,358 A | | 2/1998 | Mistretta et al. |
| 5,873,825 A | * | 2/1999 | Mistretta et al. ............ 324/307 |
| 5,879,299 A | | 3/1999 | Posse et al. |
| 5,898,305 A | | 4/1999 | Kokubun et al. |
| 6,195,579 B1 | * | 2/2001 | Carroll et al. .............. 324/306 |
| 6,275,721 B1 | * | 8/2001 | Darrow et al. .............. 324/318 |
| 6,332,088 B1 | * | 12/2001 | Zhang et al. ............... 324/307 |
| 6,400,157 B1 | * | 6/2002 | Bonanni et al. ............. 324/322 |
| 6,484,048 B1 | * | 11/2002 | Hoshino et al. ............ 600/410 |
| 2003/0036694 A1 | * | 2/2003 | Liu ............................ 600/413 |

FOREIGN PATENT DOCUMENTS

EP        1004891 A2 * 5/2000 ........... G01R/33/54

OTHER PUBLICATIONS

Functional Specifications for Fast Update Fluoroscopy, T. Hoshino, Mar. 26, 1999 (pp. 2–18).
Magnetic Resonance Imaging System, OPART™, Product Data No. MPDMR0041EBF (Apr. 2000)(pp. 1–15).

* cited by examiner

Primary Examiner—Eleni Mantis Mercader
(74) Attorney, Agent, or Firm—Nixon & Vanderhye PC

(57) ABSTRACT

The invention is an MRI imaging system that seamlessly switches between a fast imaging fluoro-mode and a diagnostic imaging mode. The fluoro-mode is used to quickly obtain an image which provides confirmation that the selection of MR imaging parameters are proper and to provide an opportunity to adjust these selections. After the selections have been confirmed and adjusted, the system is switched to a normal diagnostic image mode using the parameter selects as modified during fluoro-mode imaging.

19 Claims, 9 Drawing Sheets

APPARATUS AND METHOD FOR TRANSITION BETWEEN FLUORO-MODE AND DIAGNOSTIC MODE MAGNETIC RESONANCE IMAGING

FIELD OF THE INVENTION

This invention relates generally to magnetic resonance (MR) imaging techniques. In particular, the invention relates to seamlessly switching between fast MR fluoro and MR diagnostic imaging modes.

BACKGROUND OF THE INVENTION

Magnetic Resonance Imaging (MRI) is a widely accepted and commercially available technique for obtaining digitized visual images representing the internal structure of objects (such as the human body) having substantial populations of atomic nuclei that are susceptible to nuclear magnetic resonance (MR) phenomena. In MRI, nuclei in the body of a patient to be imaged are polarized by imposing a strong main magnetic field ($B_0$) on the nuclei. The nuclei are excited by a radio frequency (RF) signal at characteristic MR (Larmor) frequencies. By spatially distributing localized magnetic fields surrounding the body and analyzing the resulting RF responses from the nuclei, a map or image of these nuclei responses as a function of their spatial location is generated and displayed. An image of the nuclei responses provides a non-invasive view of a patient's internal organs and of other tissues.

As shown in FIG. 1, an MR imaging system typically includes a magnet 10 to impose the static magnetic field ($B_0$), gradient coils 12 for imposing spatially distributed gradient magnetic fields ($G_x$, $G_y$, and $G_z$) along three orthogonal coordinates, and RF coils 14 and 16 to transmit and receive RF signals to and from the selected nuclei of the body being imaged. The patient 18 lies on a patient table 20 such that a portion of the patient to be imaged is moved, in three-dimensions, into an "imaging volume" between the magnet and coils, which defines a field of view (FOV) of the MRI system.

The MRI system operator controls the system through a computer workstation 22 with a keyboard, screen and other operator input/output devices. The MRI system operator positions the patient within the imaging volume using a movable table 20, and selects one or more imaging parameters, such as: (a) imaging technique, e.g., diagnostic MRI, fast-MRI, MR fluoroscopy, and MR vascular imaging; (b) pulse sequence, e.g., spin echo, field echo, inversion recovery, fast spin echo and fast field echo; (c) imaging modes, e.g., multi-slice MR scans, multi-slab three-dimensional (3D) scans, multi-echo scans, multi-coverage (to cover an area greater than that covered by a single scan), and multi-angle acquisition (multiple groups of slices with different angles in the same TR); (d) fat suppression and separation techniques, and (e) artifact suppression techniques.

After the desired imaging parameters have been selected, the MRI system is programmed to scan the patient with one or more respectively corresponding pulse sequence(s) of RF pulses, slice-selection and phase encoding magnetic gradient pulses and read-out magnetic gradient field pulses. When the diagnostic scan is initiated, a predetermined pulse-sequence is repeated to generate a series of NMR RF responsive signals from the excited nuclei of the patient. The MRI system analyzes these signals and generates images of the internal organs and tissues of the patient based on the responsive RF signals.

The diagnostic MR image so generated is influenced by the selected imaging mode and imaging parameters. When the MR image is unsatisfactory or when a doctor wants to see an image from another viewpoint, another MR image is generated by adjusting the desired mode and/or selected image parameter values and then repeating the whole imaging procedure. For instance, if the contrast between two or more objects of interest shown in an MR image is not optimal, the imaging parameters for MR imaging must be adjusted to obtain proper contrast. Similarly, if the doctor judges that an axial picture obtained by MR imaging a certain portion of the head did not provide good diagnostic information, another MR image from another view point must be selected and generated.

The operator selects the desired imaging parameters before an MR image is generated. The selection of the imaging parameters determines image location, slice orientation, image quality, viewpoint and other features. It is difficult to optimally select the many imaging parameters before any image is generated. The resulting images generated from the initial parameter selections are sometimes inadequate because the selected imaging parameters are, in hindsight, less than optimal. Only by viewing an actual image does it become evident that some or all of the imaging parameter selections should be reset. However, the process of generating an MR image, resetting the imaging parameters and generating another image is excessively time consuming (e.g., several minutes), especially with diagnostic mode MR imaging techniques that require long scanning periods.

Accordingly, there is a long-felt need for a system in which the operator may quickly preview initial MR images based on the parameter selections that have currently been entered in the workstation 22. There is also a need for a technique for adjusting the diagnostic imaging parameters in view of the initial quick view images and before actually performing a longer diagnostic MRI mode. There is no known process for rapidly initially confirming that imaging parameters are properly selected for normal diagnostic MR imaging, before going through a complete diagnostic mode imaging scan.

While some real-time MR imaging techniques have been developed, they have not been applied as a tool for selecting normal (and hence slower) diagnostic scan imaging parameters. Examples of a real-time imaging process using a fast fluoro-mode imaging procedure are disclosed in U.S. Pat. Nos. 5,184,074 (Kaufman et al.) 5,898,305 (Kokubun), and 4,830,012 (Riederer).

In fluoro-mode imaging, near real-time MR images are generated using a short repetition time MRI pulse sequence. Fluoro-mode imaging has conventionally been used for MR imaging where fast imaging times are needed, such as for patient positioning within the MR imaging volume and for interventional MR imaging. While it provides fast images, fluoro-mode imaging is viewed as being inadequate for most diagnostic MR imaging purposes. See U.S. Pat. No. 5, 713,358, col. 2, lns. 1–33. Moreover, fluoro-mode imaging has not been used as a tool to expedite the selection or confirmation of imaging parameters for slower diagnostic imaging.

SUMMARY OF THE INVENTION

The present invention satisfies the above-described need for quickly confirming and adjusting diagnostic MR imaging parameters, such as, image position, orientation and alignment, and field of view (FOV), before taking the time to generate a normal diagnostic MR image. The invention enables an MRI system operator and/or associated medical practitioner to obtain quick initial MR images to confirm that the optimal imaging parameters are properly selected. In addition, the operator is able to quickly adjust the imaging parameter settings during the fast-imaging mode, if the initial settings are found to be improperly set upon viewing a fast image. Having used the fast imaging mode to confirm and/or further adjust MR imaging parameter settings, the MRI system operator can commence normal diagnostic imaging with confidence that proper image settings have been entered in the system. Accordingly, the invention provides a way to quickly confirm and adjust imaging settings for subsequent use in normal diagnostic imaging.

Using an embodiment of the invention, an MRI system operator: (a) positions a patient within the MRI imaging volume and uses a rough targeting system (e.g., projected optical cross-hairs, fluoro MR imaging, rapid batch location and other conventional acquisition locators) to align the patient within that volume; (b) selects initial imaging parameters for a particular diagnostic imaging mode; (c) switches the MRI system to a respectively corresponding "fluoro-mode" to generate a fast MR image that is used to confirm and adjust the alignment of a designed organ or other imaging target within the MRI field of view and to adjust pulse sequence and other parameters; and (e) switches back to a normal diagnostic imaging mode, using the imaging parameter selections confirmed or adjusted during fluoro-mode, to generate a complete MR image.

When switching from diagnostic-mode to fluoro-mode, the MRI system saves the original diagnostic image parameter settings that were selected by the operator for diagnostic imaging. These same imaging parameter settings that were earlier selected for diagnostic mode imaging are now automatically used (except for those settings which must be adjusted to accommodate fluoro-MRI and its speed) in a thus respectively corresponding fluoro-mode imaging mode. Using the image parameter settings selected for diagnostic imaging in a fast imaging mode provides a quick image that is useful to check the diagnostic image settings.

Not all of a given set of diagnostic image parameter settings can be used for fast imaging. To achieve fast image generation, certain of the image parameter settings are automatically converted for fast fluoro-mode, such as reducing the number of selected sequence steps and sequence slices. While in fluoro-mode, the operator may adjust some image parameter settings that were earlier selected for diagnostic imaging. When the operator then switches from fluoro-mode back to diagnostic mode imaging, the MRI system automatically applies the same imaging parameter settings that were earlier selected for diagnostic mode and that were not adjusted during fluoro-mode (many of which diagnostic settings were used in fluoro-mode imaging, while other diagnostic mode settings were automatically adjusted to correspond to fuoro-mode imaging settings), and applies to the diagnostic settings the adjustments made during fluoro-mode.

In this regard, the MRI system converts the parameter settings that were automatically changed for fluoro-mode, (e.g., number of sequence steps and slices), back to those settings originally selected for diagnostic imaging. In addition, the system also applies to diagnostic imaging parameters the adjustments that were made by the operator during fluoro-mode. Accordingly, the operator does not have to manually reset the MRI system when switching back-and-forth between diagnostic and fluoro imaging modes. The transition between modes is done effortlessly to expedite optimization of the diagnostic imaging mode settings.

BRIEF DESCRIPTION OF THE DRAWINGS

The purpose and advantages gained by the present invention will be understood better by careful study of the following detailed description of an exemplary embodiment of the invention with particular reference to the accompanying drawings, of which:

FIGS. 4A to 4D are exemplary display screen shots of MR image parameter settings for diagnostic and fluoro-mode imaging.

DETAILED DESCRIPTION OF AN EXEMPLARY EMBODIMENT

Figure 1:
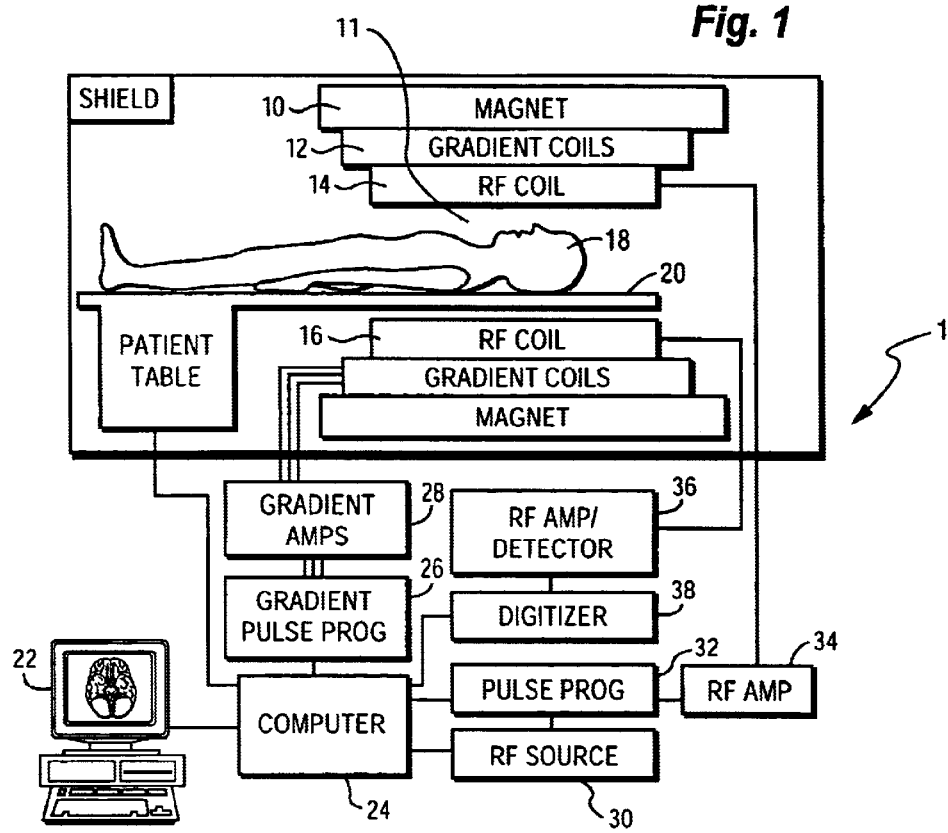
FIG. 1 is a schematic diagram of an exemplary MRI system.

FIG. 1 depicts an MRI system 1, such as the Toshiba OPART™ MRI system. An MRI system may comprise a large polarizing magnet structure 10 which generates a substantially uniform homogeneous polarizing static magnetic field ($B_0$) surrounding a patient imaging volume 11. A suitable carriage, e.g., patient table 20, inserts a portion of the anatomy of the patient 18 within the image volume 11. Magnetic gradients are selectively created by electromagnetic gradient coils 12 that are operated by an MRI sequencing processor 26. RF nuclei nutation pulses are transmitted into the patient tissue within the image volume by RF coil 14. The RF responses constituting the MR signal are received from the patient tissue via suitable RF detection coil structures 16.

The MRI system operator controls the system 1 through a computer workstation 22 with a keyboard, screen and other operator input/output devices. The MRI workstation 22 is electronically connected to a MRI computer 24 which controls the MRI system. The computer converts the image parameter selections into commands for the operation of the MRI system. In particular, the computer controls the selection of a gradient pulse program module 28 which, in turn, applies the selected magnetic pulse sequence(s) to the gradient amplifiers 28 that drive the gradient coils (or otherwise stated as the comntroller.) Similarly, the computer 24 applies RF pulses to excite the nuclei in the patient by activating an RF source 30 and an RF pulse sequence program module 32 that generates an RF pulse signal that is enhanced by amplifier 34 and applied to drive the RF drive coil 14.

The application of RF pulses, the static $B_0$ field, and the gradient slice selection and encoding pulses cause nuclei in the patient to emit MR RF signals. These analog RF signals are received by the receive coil 16, enhanced by a RF amplifier and detector 36, converted to digital image data by digitizer 38, and mathematically analyzed (such as using a Fourier analysis) by the computer/image computer 24. The analyzed image data is transformed into an image displayed on a display of the workstation 22.

The image may be a cross-sectional image of the internal organs of the patient 18. The displayed MR image is composed of picture elements called "pixels". The intensity of each pixel is proportional to the MR signal intensity of a corresponding volume element or "voxel" of the object being imaged.

Figure 2:
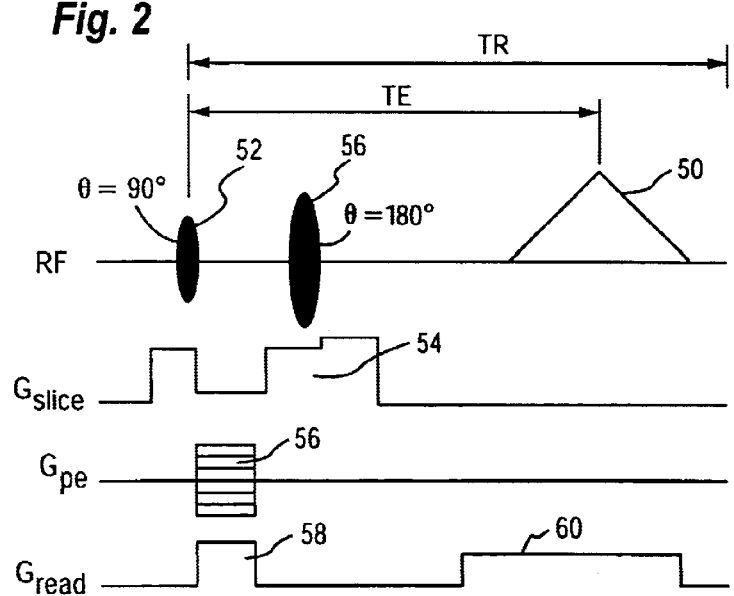
FIG. 2 is a schematic RF and gradient pulse timing diagram for an exemplary MRI pulse sequence for generating spinecho MRI responses.

In an MRI system, the various coils produces RF excitation is pulses and gradient fields to result in and acquire an MR signal during an MRI "acquisition sequence". A graphical representation of an example MRI acquisition sequence is shown in FIG. 2. In this example, the particular timing of applied RF pulses and magnetic fields is known as a "spin-echo" sequence since the MR signals appear as an "echo" 50 of a spin rotation RF pulse 52. A gradient field, $G_{slice}$, 54 is superimposed along the main field $B_0$ to sensitize a "slice" or "slab" (for 3D imaging) of nuclei in the patient's body tissue to a particular RF resonance frequency. A 180° RF excitation or "nutation" pulse, 56, is applied to refocus the nuclei within the slice or slab. Pulsed magnetic gradient fields of changing magnitudes, $G_{pe}$ (and $G_{slice}$ for 3D imaging), 56 phase encode the nuclei by inducing a temporary frequency difference and phase differences between nuclei in different locations in the body and along a specific direction within the slab. A read-out gradient field, $G_{read}$, 58 frequency encodes the nuclei in the same slice in an orthogonal direction referred to as the "readout direction" ($G_{read}$).

An MR "echo" signal, 50, resulting from the application of a read-out gradient field 60 is acquired. The echo signal induces a signal in the RF detection coil 16 that is amplified, digitized and converted to image data. The acquired data (also called "raw data" or "k-space data") is analyzed by Fourier analysis. A scaled frequency domain plot of that analysis renders information about the nuclei population after Fourier transformation to "processed data" (also referred to as the image domain), which corresponds to an X-Y-Z position.

The time period from the center of the 90° RF nutating pulse to the center of the spin-echo MR signal 50 is designated as the "echo time" (TE). The pulse sequence duration is the sequence "repetition time" (TR). There may be several repetitions applied to generate a conventional MR used for diagnosis, where each repetition has a unique phase encoding gradient value $G_{pe}$. Fast MR imaging, such as is used with fluoro-imaging, generates an image using only one or a few pulse repetitions.

With a magnetic resonance imaging apparatus of this type, MR imaging is effected as follows. The MR imaging target portion of the patient is set in a specified position within a gantry of the MRI system, usually by adjusting the position of the patient table 20. After entering relevant particulars including patient registration, the operator selects the imaging parameters, such as the RF coil and a matrix according to diagnostic items and further selects MR Imaging parameters including atomic nucleus density, relaxation time, pulse repetition time, echo time, pulse shape, pulse-sequence type, resolution, and possibly nuclide species.

The MRI workstation 22 typically presents the operator with a menu of choices for MRI sequences and data processing techniques. In the example embodiment of this invention, one of those choices available to the MRI system operator is a program for seamlessly switching to a fast fluoro-scan mode during set-up operations preceding conventional MR diagnostic imagining. The generation of a suitable computer program or such specific instructions for system computer/image processor 24 to effect the described process of the present invention is believed to be well within the ability of those skilled in the art in view of the particular data processing method described below and the totality of the disclosure set forth herein.

A MRI system, such as the Toshiba OPART™ system, may utilize several different types of MR pulse sequences, such as spin echo and field echo technologies. These sequences may support conventional imaging techniques, such as spin echo (SE), inversion recovery (IR), and two-dimensional (2D) and three-dimensional (3D) field echo (FE) techniques. In addition, MRI systems may have fast scanning sequences such as 2D fast spin echo (FastSE) with echo mapping, 3D fast field echo (FastFE) with or without RF spoiling, fast IR, fast fluid attenuated IR, fast or short TI inversion pulse period, variable TR, and variable number of signal acquisition periods (NAQ) settings.

The MRI system may include other imaging parameter settings to enable the operator to select one or more of the available imaging techniques and sequences. In addition, the system may provide options for fat suppression techniques that use multiple spin echo acquisitions with water/fat phase variations to produce fat only and/or water-only images. Another example of an imaging parameter variable is paramagnetic contrast enhancement. These imaging parameter settings, such as fat suppression and contrast enhancement, may be used in connection with one or more of the available imaging pulse sequences.

Figure 3A:
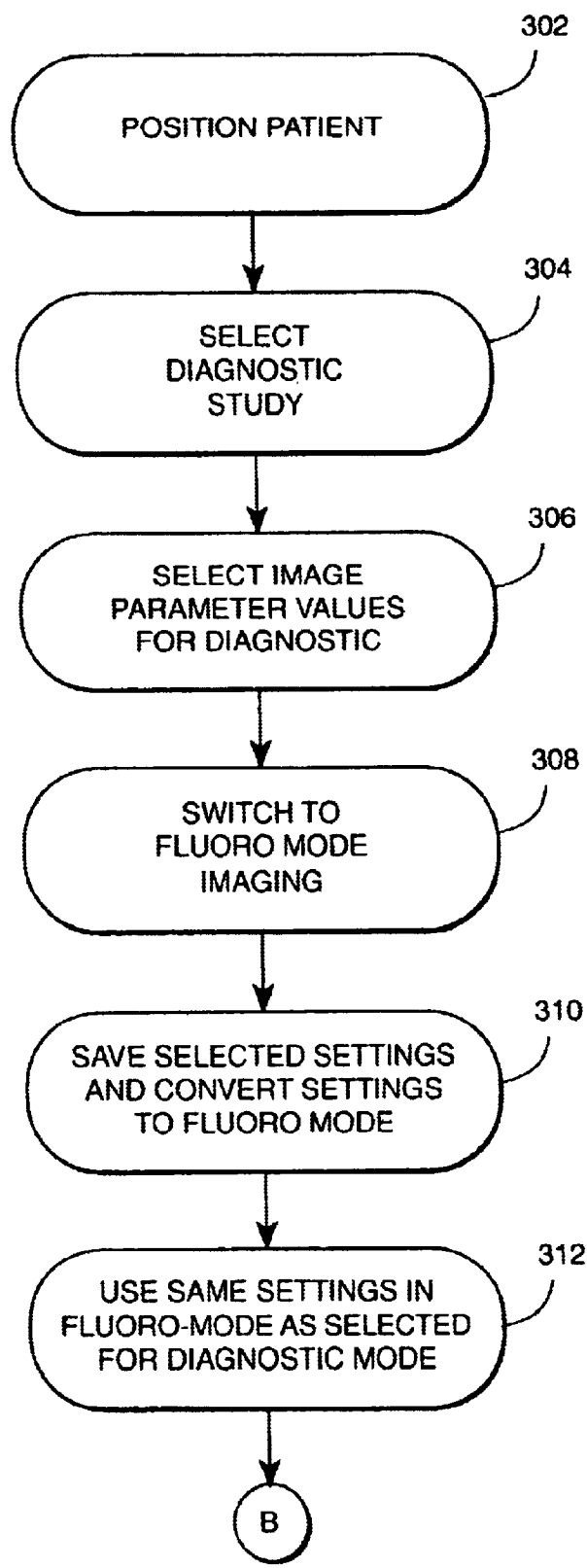
FIGS. 3A to 3C are schematic flow charts of some exemplary steps for setting MRI imaging parameters and confirming those parameters using a fluoro-scan mode as a tool.
Figure 3B:
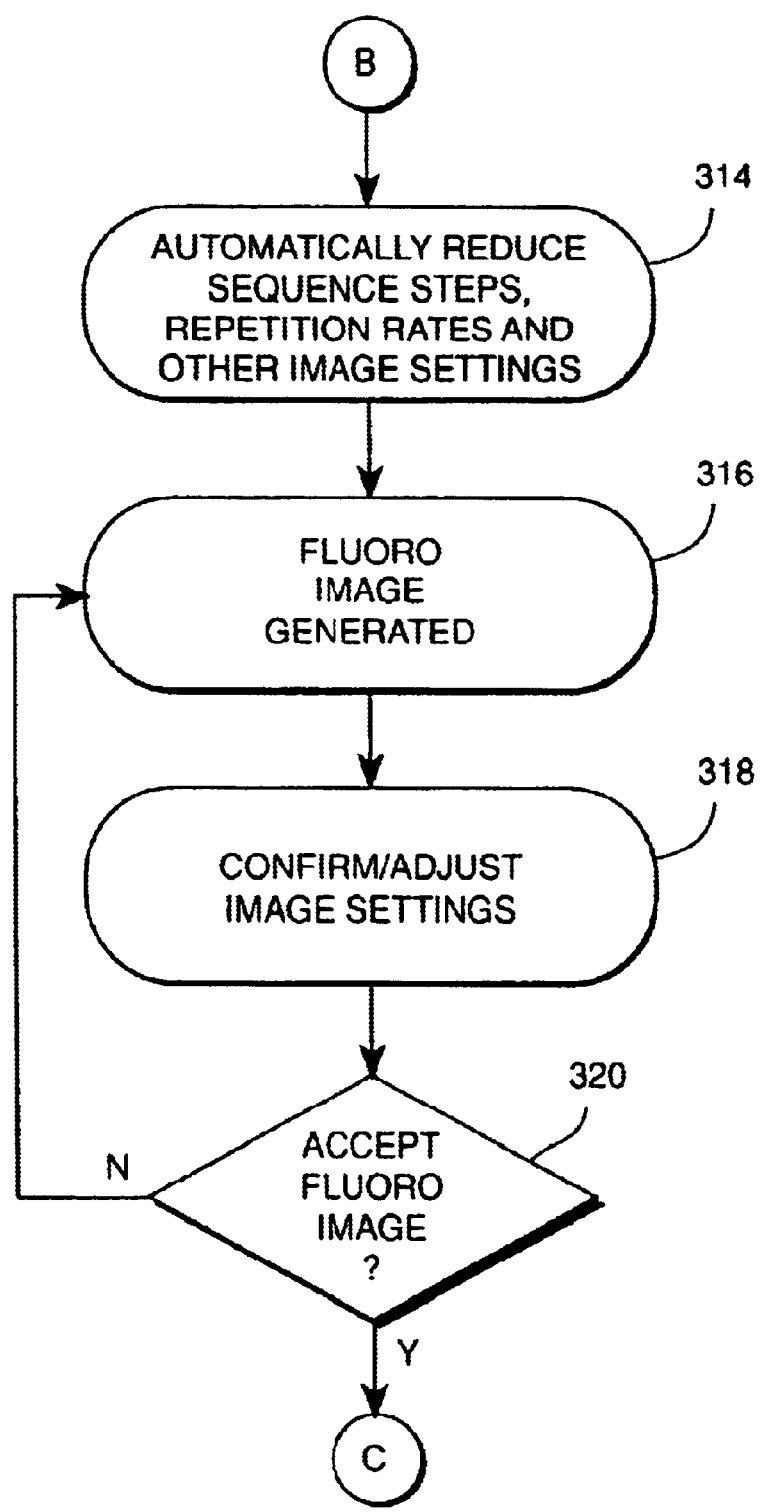
Figure 3C:
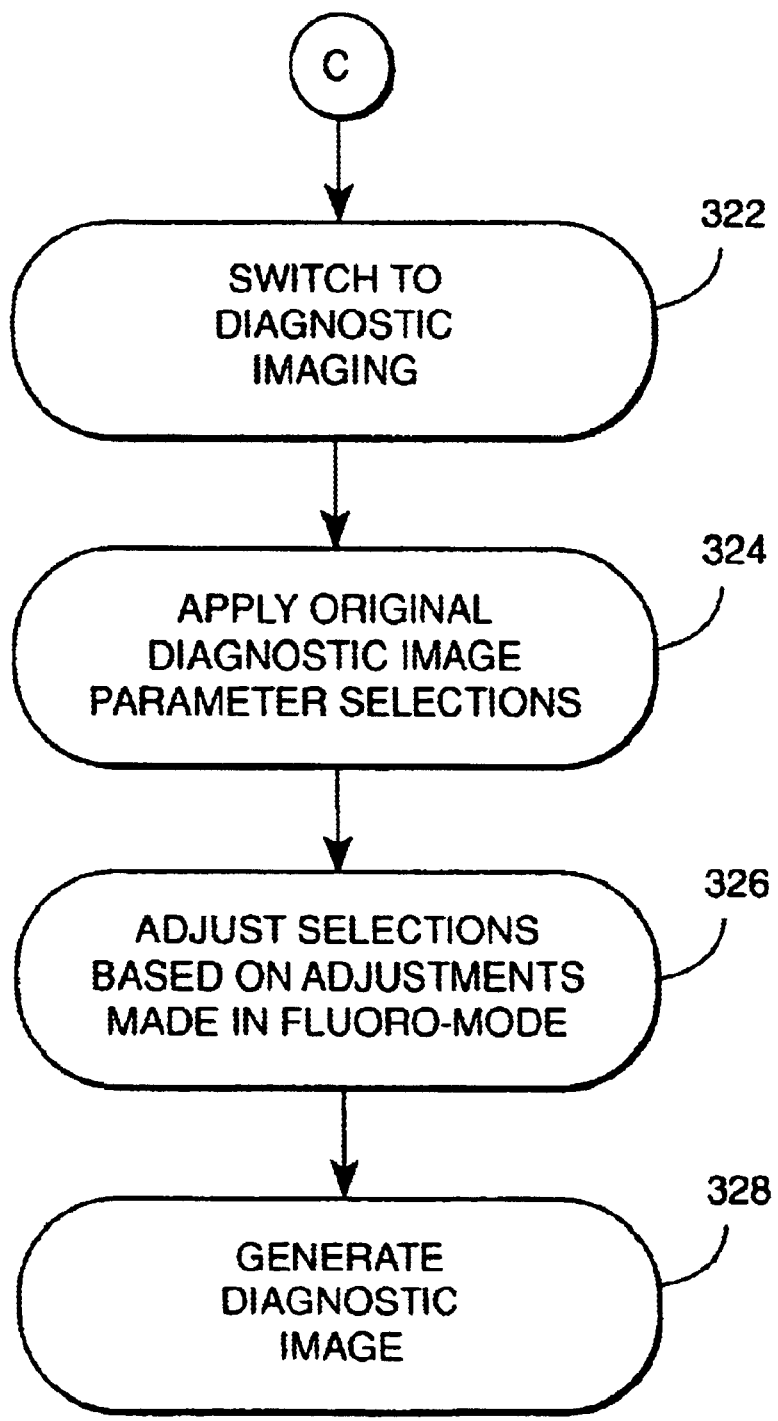

FIGS. 3A to 3C are flow charts that show an exemplary series of steps for setting-up a normal MR imaging session, using the present invention. In step 302, the patient is positioned in the MRI device. A real-time image of the patient is displayed to the operator as the patient is being positioned using fluoro MRI imaging, cross-hair lights or other quick targeting imaging means. This imaging is used to position the patient and does not utilize settings selected for diagnostic mode imaging. Once the patient has been positioned, the MRI system operator selects the MRI diagnostic imaging study to be performed in step 304.

In addition, the operator sets up the system the parameters for the selected diagnostic study (step 306), these parameters may be values for angulation, field of view, resolution, and sequence parameters such as TR, TE, TI and pulse sequence type. To set the system parameters, the operator may use the settings for an image taken from a prior MRI process (diagnostic fluoro, rapid batch acquisition) or may enter the settings directly via the work station. These parameters are selected to effect a desired MR diagnostic image. The types of pulse sequences that may be selected include spin echo, inversion recovery, 2D and 3D field echo, and other sequences. In addition, the operator may select the height and width of the field of view (FOV). The FOV may be sized within an exemplary range of 50 to 400 mm², by adjusting its height and width. The operator may also make selections for an acquisition matrix that includes parameters such as frequency encoding (e.g., between 64 to 1,024 points); phase encoding (e.g., between 32 to 1,024 lines), and slice encode direction (e.g., 8 to 256 slices). Another imaging parameter to be selected by the operator is the slice or slab thickness, e.g., between 1.0 to 100 mm for two-dimensional imaging, and between 0.8 to 100 mm for three-dimensional imaging.

Moreover, the operator selects the number of MR signal acquisitions (NAQ) from a range of, for example, 1 to 16, where the selection may be an integer or fractional increment within that range. Furthermore, scan parameters are selected such as for TR (where TR is the time period between each RF excitation pulse) having an exemplary range of 10 milliseconds (ms) to 15,000 ms; TE (which is the time to the RF echos) having an exemplary range of 10 ms to 3,000 ms; TI (which is the inversion time) having an exemplary range of 10 ms to 3,000 ms; flip angle which may have a selectable range of 0° to 180°, and b-factor (DWI)

which has an exemplary range of 101 to 1,400 s/mm². The operator may also select the appropriate slice plane, such as axial, sagittal, coronal, single oblique, double oblique, and multi-angle acquisition. These imaging setting parameters available for selection and the range of each of the selectable parameters depend on the type of diagnostic study that the operator selected in step 308. With most of the diagnostic imaging types the operator must make selections for several parameters, many having wide ranges of selectable values.

With conventional imaging methods, the operator would proceed directly to normal imaging. The invention, however, provides a fast fluoro-mode imaging selection, step 308, that the operator may use to confirm that the patient has been properly aligned in the imaging volume and that the values selected for the imaging parameters yield a high-quality MR image.

The fluoro-mode allows the operator to quickly view an image (albeit a coarse image) and adjust certain selected imaging parameters in a new real time process. The switch to a fluoro-imaging mode is performed automatically by the MRI system software that automatically converts certain of the entered imaging parameters to fluoro-imaging mode, in step 310. For example, most imaging parameters may be carried forward unaltered from the selections made for diagnostic study to fluoro-imaging, in step 312. It is preferable that most of the parameters selected for diagnostic mode imaging be carried over to fluoro-mode imaging, so that these parameter settings can be evaluated in view of a fluoro-mode image.

However, certain of the parameters selected for diagnostic imaging are automatically adjusted for fluorn-imaging, in step 314. For example, the switch to fluoro-imaging mode may result in automatic reduction in the number of phase encode steps (such as 256 lines for the phase encoding steps), in the number of readout periods (such as 256 points for readout) and in the number of slices (such as no more than 4 slices). The fluoroimaging mode is therefore preprogrammed for example to result in reduction in the number of phase encoding steps. With these adjustments, the MRI system begins imaging in fluoro-mode and quickly displays a real-time image of the body within the field of view of the imaging volume, in step 318. In view of the fluoro image, the operator confirms the image parameter settings and adjusts settings needing optimization, in step 318. The fluorn image is automatically updated to reflect adjustments made to the settings, in step 320.

Once the fluoro image is accepted, then the operator switches the MRI system back to diagnostic mode imaging in step 322. In switching to diagnostic imaging, the MRI system uses the same imaging parameters, in step 324, that were originally selected for diagnostic imaging in step 306 (including converting back to the settings automatically changed to effect fluoro-mode imaging in step 314). However, in step 326, the system automatically changes those settings from step 306 to apply the adjustments made by the operator to the settings during fluoro-mode imaging. Diagnostic imaging mode is initiated and a high-quality MR image is generated, in step 328. This image is generated by the operator, who is confident that the image parameter settings are proper after having employed the fluoro-mode imaging to check the settings. The time required to generate the diagnostic image (including the time in fluoro-mode imaging) is less than would have been required to generate a diagnostic mode image with the initial imaging parameter settings, reset the settings when the diagnostic image proved to be a disappointment, and generate a second (or third) diagnostic image using adjusted settings.

FIGS. 4A to 4D show exemplary screen images of imaging parameter settings, as would be displayed on the workstation 22. The MRI operator sets and reviews the parameter settings by interacting with the workstation display screen and keyboard, where the screen may present images such as are shown in these figures. The control screen images shown in FIGS. 4A to 4D are exemplary "scan edit" control panels used by MRI system operators to select the imaging parameters for MR imaging. Each scan edit screen shows an array of imaging parameters that may be selected for imaging. For example, the scan edit control panel 350 shown in FIG. 4A identifies several selectable imaging parameters, such as imaging techniques (FE, SE, etc. 352), options (2D, 3D, etc.) 354, TE period 356 (a selection of TE=5 in a range of 5.0 to 10.0 is shown in the figure), slice thickness 358 (seven is selected of a range of 7 to 100), and other slice parameters and many other settings. The ranges for the values of imaging parameters have been determined for each imaging mode. The range of values for each imaging parameter may vary between the different imaging modes.

The operator may adjust the settings by virtually turning the dial 360 (shown in edge view below the selectable settings) so as to change the value selected for the corresponding imaging parameter. In a preferred embodiment, the scan edit screen would show in bold font, e.g., slice thickness 358, those imaging parameters that may be changed for the selected imaging mode. Those imaging parameters that are not applicalbe to the selected mode or may not be change for the slected mode (e.g., Preset Flip Angle 362) would be shown in a shaded font on the scan edit screen.

In addition, the scan edit control screen displays the total image acquisition time 364, e.g., 1 minute and twenty seconds, image resolution, e.g., 0.52×1.00 mm, and other dependant parameters that are based on the selected imaging mode. These dependent parameters are not directly selected, but are rather determined based on the mode or values of the selectable parameters.

Figure 4A:
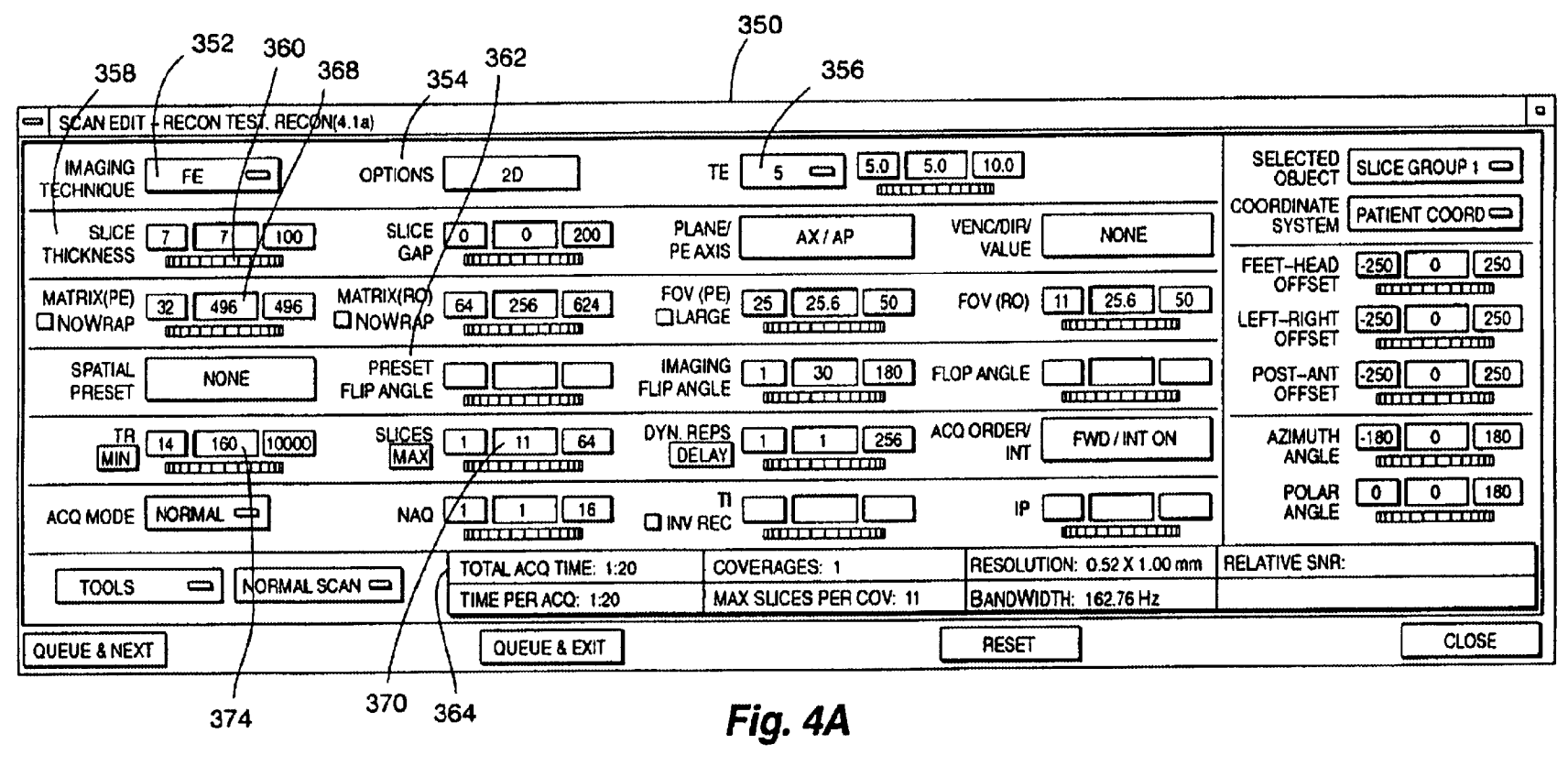
Figure 4B:
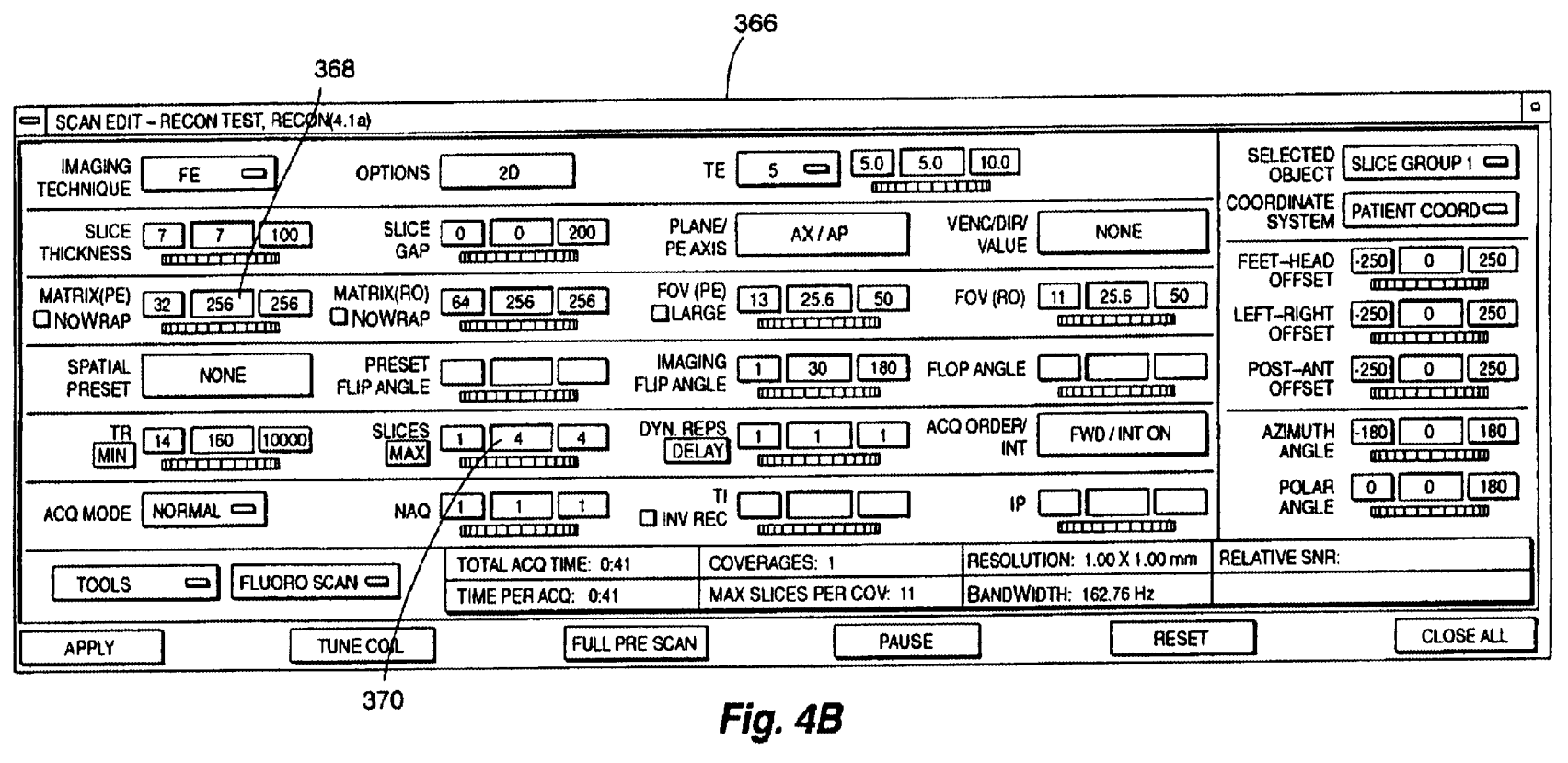

The scan edit screen image 350 shown in FIG. 4A corresponds to a diagnostic (normal) imaging mode. The values of the imaging parameters shown in FIG. 4A correspond to values selected for the diagnostic imaging mode. The values of the imaging parameters shown in FIG. 4A are those initially selected by an MRI operator, before any MR image has been reviewed. Once the initial diagnostic parameter values are selected, the operator may switch to fluoro-mode to generate a quick image based on the settings initially selected for diagnostic mode imaging. FIG. 4B shows a scan edit control screen 366 for fluoro-mode imaging. Many of the imaging parameter settings that were earlier selected for diagnostic mode imaging have been applied unchanged to fluoro-mode imaging. Those parameters settings that were automatically changed during the transition to fluoro-mode imaging are a reduction in the PE matrix 368 from 496 to 256, and a reduction in the number of slices 370 from 11 to 4.

The reduction of PE steps is arbitrary and another number of steps may have been selected. Indeed, a smaller number of PE steps provides faster flouro-imaging. In this regard, the acquisition is timed to start near the center of K-space, so that low resolution images are first generated. Higher resolution images are generated after a few TR periods. Thus, the operator may use the low resolution images generated during the initial PE steps to decide to adjust the imaging parameters and, thus, teminate the generation of the flouro image before all 256 PE steps are completed. Such a fast imaging process is disclosed in U.S. Pat. No. 4,721,912 entitled "Apparatus and Method for Initially Capturing Most Significant Low Spatial Frequency NMR Imaging Data".

In this example, the imaging parameters settings for diagnostic mode imaging were applied directly for fluoro-mode imaging, for those parameter settings within the range of selections for fluoro-mode imaging. Those diagnostic imaging settings above the range of parameter settings for fluoro-mode imaging were automatically adjusted to the maximum setting in the range for fluoro-mode imaging. For example, the PE matrix setting 368 of 256 and number of slices 370 of 4 are, in this example, the maximum values for those parameters in fluoro-mode imaging.

Figure 4C:
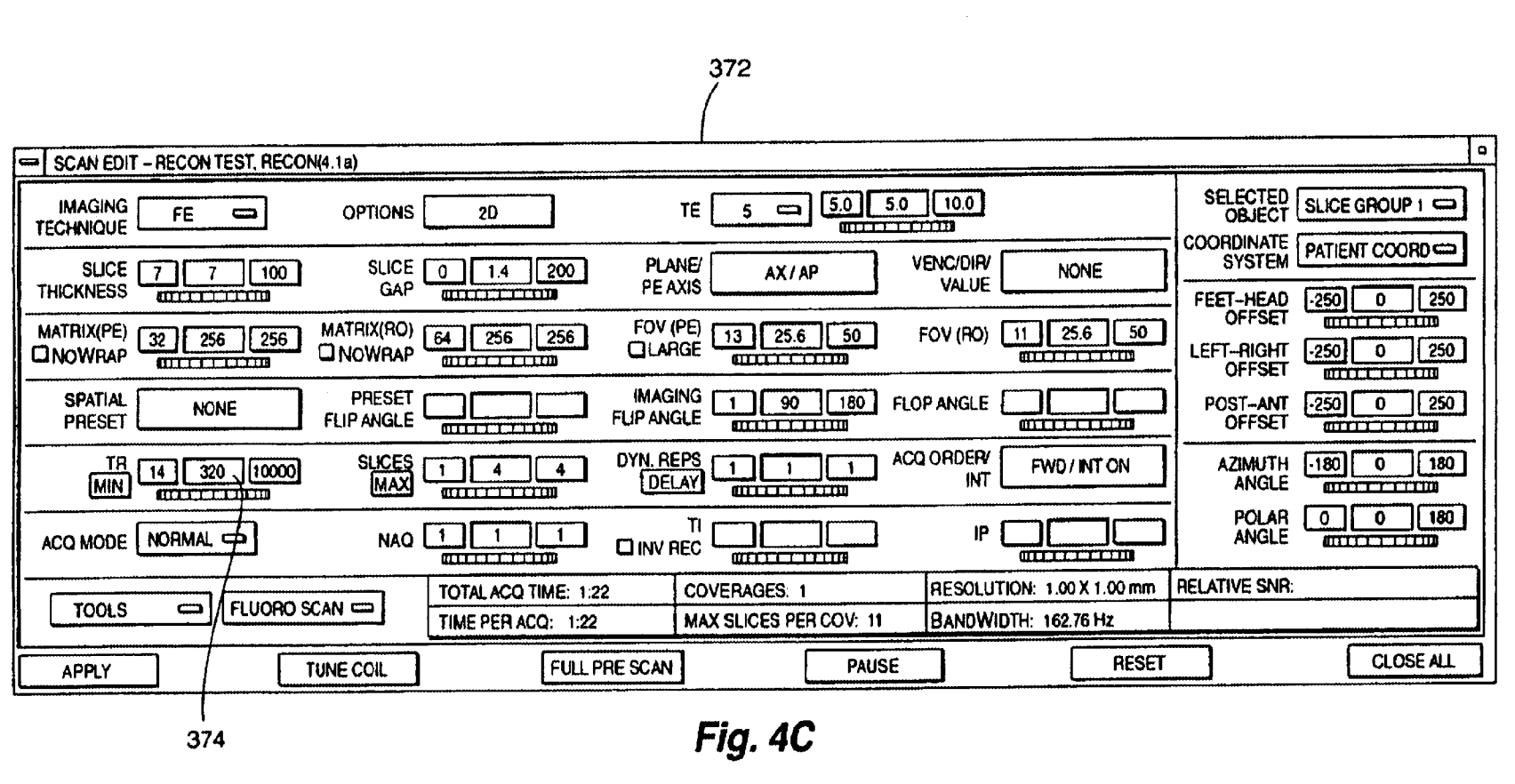

FIG. 4C shows a scan edit control screen image 372 for fluoro-mode, that is similar to the screen image shown in FIG. 4B. However, the value for TR 374 has been increased from 160 to 320. The MRI operator decided to increase in TR after viewing an MR image, e.g., FIG. 5A, generated in fluoro-mode. The value for TR 374 may have been increased to increase the contrast between the various tissues and organs shown in the image. Another MR image, e.g., FIG. 5B, is generated in fluoro-mode using the changed TR value.

When the MRI operator and/or doctor are satisfied that the imaging parameters are optimally set, the operator switches from fluoro-mode, back to diagnostic mode. With this transition, the scan edit screen, as shown in FIG. 4D, is switched to show the settings for diagnostic mode.

The same initial settings for diagnostic mode (compare FIG. 4A to FIG. 4D) have been automatically applied to the diagnostic mode, except for the image parameter settings, e.g., TR, that was changed by the operator during fluoro-mode imaging. Similarly, the imaging parameter values that were automatically changed during the transition from diagnostic mode to fluoro-mode imaging are automatically changed back to their earlier values during the transition back to diagnostic mode imaging (compare FIG. 4C to FIG. 4D with respect to the values for the PE matrix and the numberof slices).

Figure 4D:
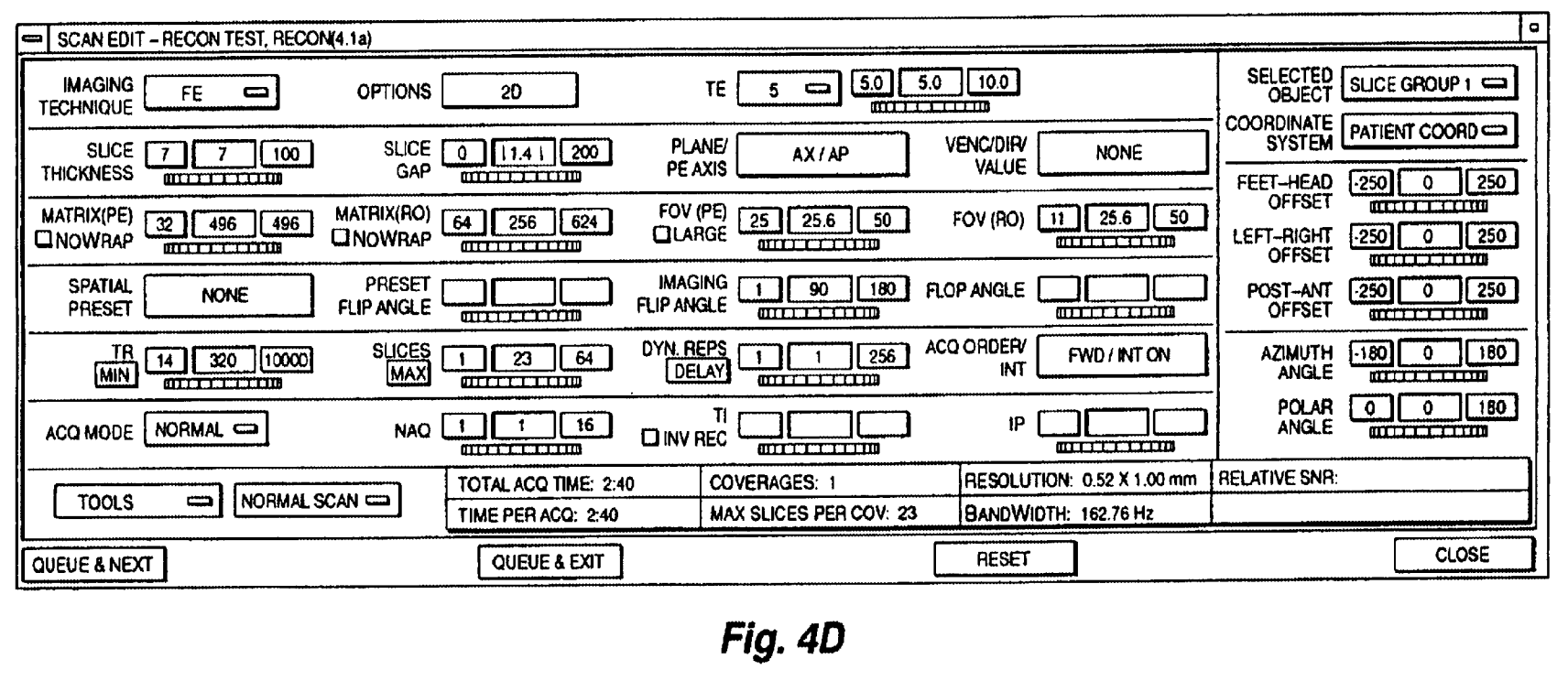

In addition, compare the acquisition time for diagnostic mode of 1 minute and 20 seconds and 2 minutes and 40 seconds, as are shown respectively in FIGS. 4A and 4D, to the fluoro-mode scan times a few seconds, e.g., 6 seconds for a TR of 320 msec (the time of 41 seconds and 1 minute 22 seconds, shown respectively in FIGS. 4B and 4C for fluoro mode represents the total fluoro MR image time which will not normally be completed for adjusting and confirming parameter settings). Accordingly, using fluoro-mode imaging in this example enabled the MRI operator to generate a first image in just a few seconds, as compared to the 1 min. 22 secs. that would have been required to generate the image using diagnostic mode imaging.

Also in this example, increasing the TR during the scan edit screen for the fluoro-mode (FIG. 4C) significantly increased the scan times for both fluoro-mode and diagnostic mode (FIG. 4D). Generating the second fluoro-mode image required 1 minute and 22 seconds. This second image was used simply to confirm that the parameter settings were optimally selected. This last fluoro-mode image (in this example, the second image) confirms the image parameter settings and, thus, instills a high degree of confidence that the settings are optimal before diagnostic mode imaging commences. Accordingly, the additional time required for the last fluoro-mode image is well spent because of the confidence gained from this image.

Figure 5A:
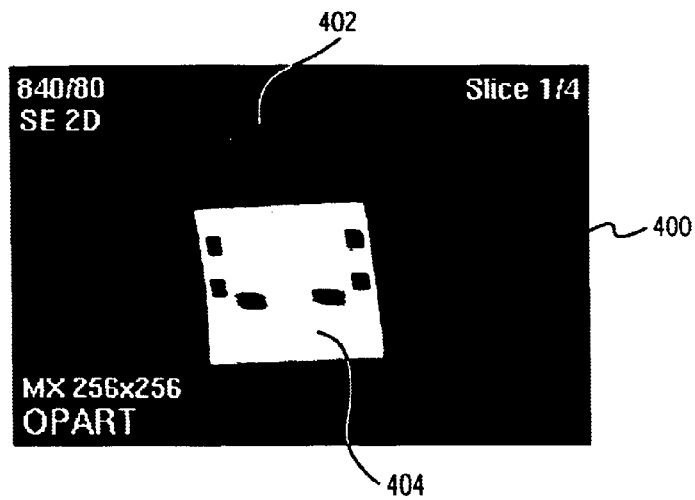
FIGS. 5A to 5C show a sequence of MR images made using (i) fluoro-imaging to confirm and adjust image parameter selections, and (ii) normal diagnostic imaging.
Figure 5B:
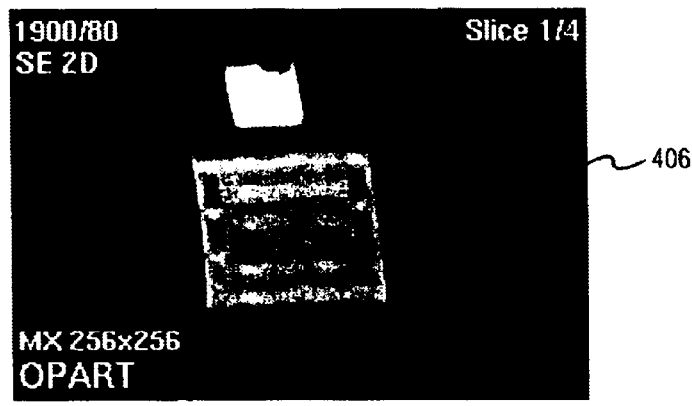
Figure 5C:

FIGS. 5A to 5C are exemplary MR Images. FIG. 5A is a fluor-mode image 400 of a oil container 402 and a water container 404. The image may be of any object(s) and would normally be an image of a patient. Several of the imaging parameters are shown in the image 400, including the TR and TE times, e.g., 840 ms for TR and 80 ms for TE; slice identification, e.g., slice one of four total slices (¼); and the acquisition matrix, e.g., 256×256 voxels. In addition, the image indicates that a 2D spin echo pulse sequence has been selected. In this example, the imaging parameters displayed on the image are the same for both the fluoro-mode and the diagnostic mode, with the exception that the number of pulse sequences and slices have been reduced for fluoro-mode. An operator viewing the image 400 shown in FIG. 5A may conclude that the contrast between the oil and water containers 402, 404 is too high and adjust the TR parameter setting to reduce the contrast. The operator adjusts the image parameter settings after viewing the imaging in fluor-mode. The operator may make several adjustments to the imaging parameters based on the fluoro-mode image. For example, the operator may adjust the image alignment with respect to the body being imaged; the periods forthe TE, TR and TI; and (other potential changes to parameters).

After the adjustments, e.g., adjusting TR to 1900 and TE to 20, a new fluoro-mode image 406 is generated, as is shown in FIG. 5B. Once the MRI system operator is satisfied with the fluoro-mode image, the system is switched back to diagnostic image mode to generate a high quality diagnostic mode image 408 in FIG. 5C . The image parameter adjustments, e.g, TR/TE of 1900/80, that were made in fluoro-mode are saved by the MRI system and used to generate the diagnostic mode image. In addition, the imaging parameter selections, e.g., number of phase encode steps and slices (7/16), has been increased from the selections (slice 1/4) used for fluoro-mode imaging.

The invention may be embodied in a software program located in the imaging control software for a MRI device. The software program stores various imaging pulse sequences and the selectable parameters associated with each sequence. The program presents to the operator options selecting the imaging mode, pulse sequence and parameters for the selected sequence. Using the program, the operator initially selects a pulse sequence and certain parameters for normal imaging mode. The operator then switches to fast fluoro-mode imaging and the software automatically converts the selected sequence to fluoro-mode by reducing the number of phase steps and slices to values appropriate for fluoro-mode operation.

While the invention has been described in connection with what is presently considered to be the most practical and preferred embodiment, it is to be understood that the, invention is not to be limited to the disclosed embodiment, but on the contrary, is intended without further analysis, to so fully reveal the gist of the present invention that others can, by applying contemporary knowledge, readily adapt it for various applications without omitting features that, from the standpoint of prior art, fairly constitute essential characteristics of the generic and specific aspects of the instant contribution to the art and, therefore, such adaptations should and are intended to be comprehended within the meaning and range of equivalence of the appended claims.

What is claimed is:

1. A magnetic resonance imaging (MRI) system comprising:
   an MRI device including an imaging volume, a magnetic field generator for applying a static magnetic field $B_0$ to the imaging volume, gradient coils for applying gradient pulses to the imaging volume, and radio frequency (RF) coils for applying RF pulses to the imaging volume and to detect nuclear magnetic resonance RF signals from a body within the imaging volume, and
   a controller for the MRI device for generating control signals to the gradient coils and radio frequency (RF) coils, and for analyzing the detected RF signals, wherein the controller includes control commands stored in a memory associated with the controller for operating the MRI device, the control commands include commands to operate the MRI device in a diagnostic MR imaging mode and in a fluoro-imaging mode, and the controller further includes:

a diagnostic-to-fluoro mode transition command to switch the MRI device from diagnostic MR imaging mode to fluoro-imaging mode by automatically applying preprogrammed fluoro-imaging mode parameters comprising diagnostic MR imaging mode parameters modified to effect fluoro-imaging mode, manual operator activated controls for adjusting any of said diagnostic MR imaging mode pameters modified to effect fluoro-imaging mode to obtain enhanced images, and a fluoro-to-diagnostic mode transition command to switch the MRI device from fluoro-imaging mode to diagnostic MR imaging mode by automatically applying the diagnostic MR imaging mode parameters that were autmotical modified during fluoro-imaging mode and any of the diagnostic MR imaging mode parameters which were modified by the manual operator activated controls.

2. A magnetic resonance imaging control system for a magnetic resonance imaging (MRI) system, said control system comprising:

a preprogrammed controller for switching from a diagnostic MRI mode to a fluoro-mode MRI by automatically switching diagnostic MRI sequence parameters to fluoro-mode MRI sequence parameters; and input means for adjusting MRI sequence parameters to obtain enhanced images during fluoro-mode MRI;

wherein said preprogrammed controller when subsequently switched back to the diagnostic MRI mode uses sequence parameters corresponding to the MRI sequence parameters as adjusted during said fluoro-mode MRI.

3. A control system as claimed in claim 2, wherein said preprogrammed controller, in said subsequent diagnostic MRI mode, uses the MRI sequence parameters that were not adjusted during said fluoro-mode MRI and the sequence parameters that were adjusted during said fluoro-mode MRI.

4. A method for quickly conforming and adjusting imaging settings for obtaining a magnetic resonance image, in which an image sequence is preprogrammed into a computer controller, said method comprising:

a. selecting magnetic resonance imaging (MRI) parameter settings for a diagnostic MR imaging mode;

b. choosing a preprogrammed fluoro mode for said image sequence;

c. automatically changing particular parameter settings selected for the diagnostic MR imaging mode to effect the preprogrammed fluoro-mode;

d. automatically recording the particular parameter settings changed to effect fluoro-mode imaging;

e. generating an MR image using the magnetic resonance imaging (MRI) parameter settings selected in (a) as changed in (c);

f. adjusting selected ones of the mganetic resonance imaging (MRI) parameter settings in view of the generated MR image;

g. switching back to the diagnostic MR imaging mode; and h. automatically returning the magnetic resonance imaging (MRI) parameter settings to the values in (a) as adjusted in (f) to thereby modify the magnetic resonance imaging (MRI) parameter settings for the diagnostic MR imaging mode.

5. The method of claim 4 wherein the preprogrammed parameter settings changed in (c) comprise a group that includes at least one of; (i) a number of phase encoding steps, (ii) a number of slices and (iii) a number of readout points.

6. The method of claim 4 including repeatedly making manual adjustments to the parameter settings and performing (d), (e) and (f) until an acceptable fluoro-mode image is generated.

7. The method of claim 4 wherein (a) and (b) are performed sequentially.

8. The method of claim 4 wherein (b) is performed prior to (a).

9. The method in claim 4 wherein in (g) and (h) at least one of the parameter settings changed in (c) is automatically returned to the parameter settings in (a).

10. The method of claim 4 wherein said selected MRI parameter settings include the spatial position of the body to be imaged within an MRI field of view.

11. A method as in claim 4 wherein during (e) fluoro-mode images suitable for previewing and adjusting parameter settings are generated before the fluoro-mode imaging is completed.

12. A method as in claim 4 wherein during (e) the fluoro-mode imaging includes starting an acquisition process from or near a center of k-space.

13. A method as in claim 12 wherein during (e) fluoro-mode imaging is terminated before a complete set of k-space data is acquired.

14. A method for quickly conforming and adjusting imaging settings for obtaining a magnetic resonance image, in which an image sequence is preprogrammed into a computer controller, said method comprising:

a. selecting MRI imaging parameters for a diagnostic (MR) imaging mode;

b. choosing a fast MRI mode for said image sequence;

c. automatically changing particular imaging parameters selected for the diagnostic imaging mode to effect the preprogrammed fast MRI mode;

d. automatically recording the selected imaging parameters changed to effect the fast MRI mode;

e. generating a MR image using the MRI imaging parameters selected in (a) as changed in (c);

f. adjusting selected ones of the MRI imaging parameters in view of the generated MR image;

g. switching back to the diagnostic (MR) imaging mode; and h. automatically returning the MRI imaging parameters to the values in (a) as adjusting in (f) to thereby modify the MRI imaging parameter for the diagnostic (MR) imaging mode.

15. A method for quickly conforming and adjusting imaging settings for obtaining a magnetic resonance image, in which an image sequence is preprogrammed into a computer controller, said method comprising:

a. selecting MRI parameters for a diagnostic (MR) imaging mode to create selecte MRI parameters;

b. choosing a fluoro-mode for said image sequence;

c. automatically changing at least some of the selected MRI parameters to effect the pre-programmed fluoro-mode and generating fluoro-mode images;

d. manually adjusting at least some of the selected MRI parameters in view of the fluoro-mode images;

e. switching from the preprogrammed fluoro-mode back to the diagnostic (MR) imaging mode, including automatically applying the selected MRI parameters as modified in (d) to the diagnostic (MR) imaging mode, and f. generating a diagnostic MR image using the selected MRI parameters in (a) as manually adjusted in (d).

16. A method as in claim 15, wherein (c) includes switching to the preprogrammed fluoro-mode, and the selected MRI parameters for the diagnostic (MR) imaging mode are automatically changed to effect the preprogrammed fluoro-mode.

17. A method as in claim 15, wherein (e) includes switching from the preprogrammed fluoro-mode back to the diagnostic (MR) imaging mode and the selected MRI parameters that were not manually adjusted in (d) are automatically readjusted to effect the diagnostic (MR) imaging mode.

18. A method for automatically adjusting MRI sequence parameters for diagnostic MRI based on related adjustment of fluoro-mode MRI sequence parameters, said method comprising:

a) performing fluoro-mode MRI using sequence parameters corresponding to a selected diagnostic MRI mode and permitting adjustment of said sequence parameters while operating in fluoro-mode MRI; and b) subsequently performing diagnostic MRI in the diagnostic MRI mode automatically using sequence parameters corresponding to the sequence parameters as adjusted during said fluoro-mode MRI.

19. A method as claimed in claim 18, wherein said subsequently performed diagnostic MRI involves using the sequence parameters that were not adjusted during said performed fluoro-mode MRI and the sequence parameters that were adjusted during said performed fluoro-mode MRI.

* * * * *